(12) United States Patent
Ye et al.

(10) Patent No.: US 9,549,971 B2
(45) Date of Patent: Jan. 24, 2017

(54) METHODS FOR INHIBITING ANGIOGENESIS USING EGFL8 ANTAGONISTS

(75) Inventors: Weilan Ye, Foster City, CA (US); Han Lu, San Bruno, CA (US)

(73) Assignee: GENENTECH, INC., South San Francisco, CA (US)

( * ) Notice: Subject to any disclaimer, the term of this patent is extended or adjusted under 35 U.S.C. 154(b) by 276 days.

(21) Appl. No.: 12/812,944

(22) PCT Filed: Jan. 14, 2009

(86) PCT No.: PCT/US2009/030969
§ 371 (c)(1),
(2), (4) Date: Aug. 30, 2010

(87) PCT Pub. No.: WO2009/091810
PCT Pub. Date: Jul. 23, 2009

(65) Prior Publication Data
US 2011/0014194 A1     Jan. 20, 2011

Related U.S. Application Data

(60) Provisional application No. 61/020,960, filed on Jan. 14, 2008.

(51) Int. Cl.
| | |
|---|---|
| *A61K 6/00* | (2006.01) |
| *A61K 39/00* | (2006.01) |
| *A61K 39/395* | (2006.01) |
| *C07K 1/00* | (2006.01) |
| *C07K 16/00* | (2006.01) |
| *C07K 16/18* | (2006.01) |
| *C07K 16/22* | (2006.01) |
| *A01K 67/027* | (2006.01) |
| *C07K 14/485* | (2006.01) |
| *C12N 15/85* | (2006.01) |

(52) U.S. Cl.
CPC ....... *A61K 39/0005* (2013.01); *A01K 67/0276* (2013.01); *A61K 39/395* (2013.01); *C07K 14/485* (2013.01); *C12N 15/8509* (2013.01); *A01K 2217/075* (2013.01); *A01K 2227/105* (2013.01); *A01K 2267/0375* (2013.01)

(58) Field of Classification Search
CPC ........ A61K 6/00; A61K 39/00; A61K 39/395; A61K 39/39533; A61K 39/39558; A61K 2008/00; A61K 2039/00; A61K 2039/505; A61K 2039/507; C07K 1/00; C07K 16/00; C07K 16/18; C07K 16/22
See application file for complete search history.

(56) References Cited

U.S. PATENT DOCUMENTS

| | | | |
|---|---|---|---|
| 2003/0166907 A1* | 9/2003 | Sheppard et al. | ........... 536/23.5 |
| 2003/0180784 A1* | 9/2003 | McCarthy et al. | ............... 435/6 |
| 2007/0031437 A1 | 2/2007 | Filvaroff et al. | |
| 2012/0003208 A1 | 1/2012 | Filvaroff et al. | |

FOREIGN PATENT DOCUMENTS

| | | |
|---|---|---|
| JP | 2007-532685 A | 11/2007 |
| RU | 2257911 C2 | 8/2005 |
| WO | WO-01/12210 A1 | 2/2001 |
| WO | 2004/013292 A2 | 2/2004 |
| WO | 2005-117968 A2 | 12/2005 |
| WO | WO-2006/049854 A2 | 5/2006 |
| WO | WO-2006/049854 A3 | 5/2006 |
| WO | WO 2008/021290 * | 2/2008 |

OTHER PUBLICATIONS

Tanaka listed in UniProt/SWISS-PROT1 Database: EGFL8_HUMAN (submitted Sep. 2004).*
Lynch et al. Bevacizumab for neovascular ocular diseases. The Annals of Pharmacotherapy 41: 614-625, published online Mar. 13, 2007.*
Campagnolo et al., "EGFL7 is a chemoattractant for endothelial cells and is up-regulated in angiogenesis and arterial injury" *Am J Pathol.* 167(1):275-84 (Jul. 2005).
Database accession No. Q99944, "Epidermal growth factor-like protein 8" *Database UniProt* pp. 6 pages, Oct. 5, 2010.
Duda et al., "Antiangiogenics: the potential role of integrating this novel treatment modality with chemoradiation for solid cancers" *Journal of Clinical Oncology* 25(26):4033-42 (Sep. 10, 2007).
Ferrara and Davis-Smyth, "The Biology of Vascular Endothelial Growth Factor" *Endocrine Reviews* 18(1):4-25 (1997).
Fitch et al., "Egfl7, a novel epidermal growth factor-domain gene expressed in endothelial cells" *Dev Dyn.* 230(2):316-324 (Jun. 2004).
Kesisis et al., "Angiogenesis inhibitors, drug selectivity and target specificity" *Current Pharmaceutical Design* 13:2795-2809 (2007).
Parker et al., "The endothelial-cell-derived secreted factor Egfl7 regulates vascular tube formation" *Nature* 428(6984):754-758 (Apr. 15, 2004).
Schmidt et al., "EGFL7 regulates the collective migration of endothelial cells by restricting their spatial distribution" *Development* 134(16):2913-23 (Aug. 2007).
Schmidt et al., "The role of Egfl7 in vascular morphogenesis" *Novartis Foundation Symposium* 283:18-28 (2007).
Zhang et al., "Ocular neovascularaization: Implication of endogenous angiogenic inhibitors and potential therapy" *Progress in Retinal and Eye Research* 26:1-37 (2007).
D'Amato, R.J. et al. (Apr. 1994). "Thalidomide is an Inhibitor of Angiogenesis," *Proc. Natl. Acad. Sci. USA* 91;4082-4085.
Klauber, N. (Nov. 15, 1996). "New Activity of Spironolactone. Inhibition of Angiogenesis in Vitro and in Vivo," *Circulation* 94(10):2566-2571, seven pages.

(Continued)

*Primary Examiner* — Alana Harris Dent
(74) *Attorney, Agent, or Firm* — Morrison & Foerster LLP

(57) ABSTRACT

The present invention provides methods of using EGFL8 antagonists to inhibit vascular development and to treat related disorders.

7 Claims, 4 Drawing Sheets

(56) References Cited

OTHER PUBLICATIONS

Liao, F. et al. (May 1, 2002). "Selective Targeting of Angiogenic Tumor Vasculature by Vascular Endothelial-Cadherin Antibody Inhibits Tumor Growth Without Affecting Vascular Permeability," *Cancer Research* 62:2567-2575.

Ridgway, J. et al. (Dec. 21, 2006). "Inhibition of Dll4 Signalling Inhibits Tumour Growth by Deregulating Angiogenesis," *Nature* 444(7122):1083-1087.

\* cited by examiner

E10.5 Mouse Embryonic Cranial Vasculatures

*Egfl8* / Arterial Branches

E10.5 Mouse Embryonic Cranial Vasculatures

*Egfl7* / Most Vessels

Egfl8 Knockout Vascular Phenotype in the Retina

Isolectin B4 Stained P8 Mouse Retina

Egfl7 +/-, Egfl8 -/-       Egfl7 -/-, Egfl8 -/-

Isolectin B4 Stained P8 Mouse Retina

Egfl7 +/-, Egfl8 -/-       Egfl7 -/-, Egfl8 -/-

SEQUENCE LISTING

```
<160> NUMBER OF SEQ ID NOS: 4

<210> SEQ ID NO 1
<211> LENGTH: 293
<212> TYPE: PRT
<213> ORGANISM: Homo sapiens

<400> SEQUENCE: 1

Met Gly Ser Arg Ala Glu Leu Cys Thr Leu Leu Gly Gly Phe Ser
 1               5                  10                  15

Phe Leu Leu Leu Ile Pro Gly Glu Gly Ala Lys Gly Gly Ser
                20                  25                  30

Leu Arg Glu Ser Gln Gly Val Cys Ser Lys Gln Thr Leu Val Val
                35                  40                  45

Pro Leu His Tyr Asn Glu Ser Tyr Ser Gln Pro Val Tyr Lys Pro
                50                  55                  60

Tyr Leu Thr Leu Cys Ala Gly Arg Arg Ile Cys Ser Thr Tyr Arg
                65                  70                  75

Thr Met Tyr Arg Val Met Trp Arg Glu Val Arg Arg Glu Val Gln
                80                  85                  90

Gln Thr His Ala Val Cys Cys Gln Gly Trp Lys Lys Arg His Pro
                95                 100                 105

Gly Ala Leu Thr Cys Glu Ala Ile Cys Ala Lys Pro Cys Leu Asn
                110                 115                 120

Gly Gly Val Cys Val Arg Pro Asp Gln Cys Glu Cys Ala Pro Gly
                125                 130                 135

Trp Gly Gly Lys His Cys His Val Asp Val Asp Glu Cys Arg Thr
                140                 145                 150

Ser Ile Thr Leu Cys Ser His His Cys Phe Asn Thr Ala Gly Ser
                155                 160                 165

Phe Thr Cys Gly Cys Pro His Asp Leu Val Leu Gly Val Asp Gly
                170                 175                 180

Arg Thr Cys Met Glu Gly Ser Pro Glu Pro Thr Ser Ala Ser
                185                 190                 195

Ile Leu Ser Val Ala Val Arg Glu Ala Glu Lys Asp Glu Arg Ala
                200                 205                 210

Leu Lys Gln Glu Ile His Glu Leu Arg Gly Arg Leu Glu Arg Leu
                215                 220                 225

Glu Gln Trp Ala Gly Gln Ala Gly Ala Trp Val Arg Ala Val Leu
                230                 235                 240

Pro Val Pro Pro Glu Glu Leu Gln Pro Glu Gln Val Ala Glu Leu
                245                 250                 255

Trp Gly Arg Gly Asp Arg Ile Glu Ser Leu Ser Asp Gln Val Leu
                260                 265                 270

Leu Leu Glu Glu Arg Leu Gly Ala Cys Ser Cys Glu Asp Asn Ser
                275                 280                 285

Leu Gly Leu Gly Val Asn His Arg
                290
```

```
<210> SEQ ID NO 2
<211> LENGTH: 293
<212> TYPE: PRT
<213> ORGANISM: Mus musculus

<400> SEQUENCE: 2

Met Gly Leu Trp Ala Glu Leu Cys Ile Ser Leu Arg Gly Leu Ser
 1               5                  10                  15

Phe Phe Leu Val Leu Met Thr Gly Glu Gly Thr Arg Gly Gly Ser
                20                  25                  30

Phe Lys Glu Ser Leu Gly Val Cys Ser Lys Gln Thr Leu Leu Val
                35                  40                  45

Pro Leu Arg Tyr Asn Glu Ser Tyr Ser Gln Pro Val Tyr Lys Pro
                50                  55                  60

Tyr Leu Thr Leu Cys Ala Gly Arg Arg Ile Cys Ser Thr Tyr Arg
                65                  70                  75

Thr Thr Tyr Arg Val Ala Trp Arg Glu Val Arg Arg Glu Val Pro
                80                  85                  90

Gln Thr His Val Val Cys Cys Gln Gly Trp Lys Lys Pro His Pro
                95                 100                 105

Gly Ala Leu Thr Cys Asp Ala Ile Cys Ser Lys Pro Cys Leu Asn
               110                 115                 120

Gly Gly Val Cys Thr Gly Pro Asp Arg Cys Glu Cys Ala Pro Gly
               125                 130                 135

Trp Gly Gly Lys His Cys His Val Asp Val Asp Glu Cys Arg Ala
               140                 145                 150

Ser Leu Thr Leu Cys Ser His Gly Cys Leu Asn Thr Leu Gly Ser
               155                 160                 165

Phe Leu Cys Ser Cys Pro His Pro Leu Val Leu Gly Leu Asp Gly
               170                 175                 180

Arg Thr Cys Ala Gly Gly Pro Pro Glu Ser Pro Thr Ser Ala Ser
               185                 190                 195

Ile Leu Ser Val Ala Val Arg Glu Ala Asp Ser Glu Glu Glu Arg
               200                 205                 210

Ala Leu Arg Trp Glu Val Ala Glu Leu Arg Gly Arg Leu Glu Lys
               215                 220                 225

Leu Glu Gln Trp Ala Thr Gln Ala Gly Ala Trp Val Arg Ala Val
               230                 235                 240

Leu Pro Met Pro Pro Glu Glu Leu Arg Pro Glu Gln Val Ala Glu
               245                 250                 255

Leu Trp Gly Arg Gly Asp Arg Ile Glu Ser Leu Ser Asp Gln Val
               260                 265                 270

Leu Leu Leu Glu Glu Arg Leu Gly Ala Cys Ala Cys Glu Asp Asn
               275                 280                 285

Ser Leu Gly Pro Ser Leu Arg Gly
               290

<210> SEQ ID NO 3
<211> LENGTH: 1337
<212> TYPE: DNA
<213> ORGANISM: Mus musculus

<400> SEQUENCE: 3
gtagggctct gccgggacct gggtcttccc tctcctggag ctgcagaggc         50
cagaagttca gtggtgaggg gtccaaggag agtccgggga gaccagggag        100
```

| | |
|---|---|
| gctctgtcca tccctgtcc ctgtccctgt gggaagcccc cggcagcagc | 150 |
| aagacgctgg ctgttccacc tgcccacaag aacagccacc accagtaccc | 200 |
| aggggatgac aagcggccgg accacaggcc acaaaaagaa gaaggctacc | 250 |
| ccacttacag atgcagacca tgtggggctc cggagaactg cttgtagcat | 300 |
| ggtttctagt gttggcagca gatggtacta ctgagcatgt ctacagaccc | 350 |
| agccgtagag tgtgtactgt ggggatttcc ggaggttcca tctcggagac | 400 |
| ctttgtgcag cgtgtatacc agccttacct caccacttgc gacggacaca | 450 |
| gagcctgcag cacctaccga accatctacc ggactgccta tcgccgtagc | 500 |
| cctggggtga ctcccgcaag gcctcgctat gcttgctgcc ctggttggaa | 550 |
| gaggaccagt gggctcctg gggcttgtgg agcagcaata tgccagcctc | 600 |
| catgtgggaa tggagggagt tgcatccgcc caggacactg ccgctgccct | 650 |
| gtgggatggc agggagatac ttgccagaca gatgttgatg aatgcagtac | 700 |
| aggagaggcc agttgtcccc agcgctgtgt caatactgtg gaagttact | 750 |
| ggtgccaggg atgggaggga caaagcccat ctgcagatgg gacgcgctgc | 800 |
| ctgtctaagg aggggccctc cccggtggcc caaaccccca cagcaggagt | 850 |
| ggacagcatg gcgagagagg aggtgtacag gctgcaggct cgggttgatg | 900 |
| tgctagaaca gaaactgcag ttggtgctgg ccccactgca cagcctggcc | 950 |
| tctcggtcca cagagcatgg gctacaagat cctggcagcc tgctggccca | 1000 |
| ttccttccag cagctggacc gaattgattc actgagtgag caggtgtcct | 1050 |
| tcttggagga acatctgggg tcctgctcct gcaaaaaaga tctgtgataa | 1100 |
| cctctcacca cccaggctgg atagagcagt catccctaga tcccttgtag | 1150 |
| ccagagttca ggcgctgtct ggtggtgcct atgagcagaa ggccctgcct | 1200 |
| cattgtccct ctttcttagg aggttcctag gacttgggca tggggagtgg | 1250 |
| ggtcttgtgt gactcttcag tggggctccc tgtctaagtg gtaaggtggg | 1300 |
| gattgtctcc atctttgtca taataaagct gagactt | 1337 |

<210> SEQ ID NO 4
<211> LENGTH: 501
<212> TYPE: DNA
<213> ORGANISM: Mus musculus

<400> SEQUENCE: 4

| | |
|---|---|
| ggaggatctt tcaaagagag tttgggagtg tgctccaagc agacgctgct | 50 |
| ggttcctctc cgttacaacg agtcctatag tcaaccggtg tacaaaccct | 100 |
| acctgacctt gtgtgcgggg aggcgcatat gtagcaccta caggaccaca | 150 |
| taccgtgtgg cctggcggga ggtgaggcgg gaggtaccac agacacacgt | 200 |
| ggtgtgctgt cagggctgga agaagccaca cccaggagct ctcacctgtg | 250 |
| atgccatctg ctccaagcct tgtcttaatg gaggtgtctg cactggacca | 300 |
| gaccggtgcg agtgtgcccc aggctgggga ggaaagcatt gccacgtgga | 350 |
| tgtcgatgaa tgcagggcca gccttaccct ctgctctcat ggctgcctca | 400 |
| acacactggg cagcttcttg tgcagctgtc cacacccct ggtgctgggt | 450 |

```
                                                    -continued
ctcgatggac gcacctgtgc aggaggccca ccggagagtc caaccagcgc           500
g                                                                501
```

METHODS FOR INHIBITING ANGIOGENESIS USING EGFL8 ANTAGONISTS

CROSS REFERENCE TO RELATED APPLICATION

This application is a National Stage application of International Application No. PCT/US2009/030969, filed Jan. 14, 2009, which claims priority under 35 USC 119(e) to provisional application No. 61/020,960, filed 14 Jan. 2008, the disclosure of which is incorporated herein by reference in its entirety.

FIELD OF THE INVENTION

The present invention relates generally to compositions and methods that are useful for treatment of conditions and diseases associated with angiogenesis. Specifically, the present invention relates to antagonists of EGF-like domain 8 (EGFL8).

BACKGROUND OF THE INVENTION

It is now well established that angiogenesis is an important contributor to the pathogenesis of a variety of disorders. These include solid tumors and metastasis, atherosclerosis, retrolental fibroplasia, hemangiomas, chronic inflammation, intraocular neovascular diseases such as proliferative retinopathies, e.g., diabetic retinopathy, retinal vein occlusion (RVO), age-related macular degeneration (AMD), neovascular glaucoma, immune rejection of transplanted corneal tissue and other tissues, rheumatoid arthritis, and psoriasis. Duda et al. *J. Clin. Oncology* 25(26): 4033-42 (2007); Kesisis et al. *Curr. Pharm. Des.* 13: 2795-809 (2007); Zhang & Ma *Prog. Ret. & Eye Res.* 26: 1-37 (2007).

In the case of tumor growth, angiogenesis allows tumor cells to acquire a growth advantage and proliferative autonomy compared to normal cells. A tumor usually begins as a single aberrant cell which is able to grow only to a size of a few cubic millimeters due to the distance from available capillary beds and it can stay 'dormant' without further growth or dissemination for a long period of time. Some tumor cells then switch to the angiogenic phenotype to activate endothelial cells (ECs), which proliferate and mature into new capillary blood vessels. These newly formed blood vessels not only allow for continued growth of the primary tumor, but also for the dissemination and recolonization of metastatic tumor cells. The mechanisms that control the angiogenic switch are not well understood, but it is believed that neovascularization of tumor mass results from the net balance of a multitude of angiogenesis stimulators and inhibitors.

To date, a significant number of molecules, mostly secreted factors produced by surrounding cells, have been shown to regulate EC differentiation, proliferation, migration and coalescence into cord-like structures. For example, vascular endothelial growth factor (VEGF) has been identified as the key factor involved in stimulating angiogenesis and in inducing vascular permeability. Ferrara et al., *Endocr. Rev.* 18:4-25 (1997). In addition, an ECM-associated protein designated epidermal growth factor-like 7 (EGFL7) has been shown to be expressed by endothelial cells and to have a role in angiogenesis. Parker et al., *Nature* 428: 754-58 (2004); Fitch et al., *Dev. Dynamics* 230: 316-24 (2004); Campagnolo et al., *Am. J Path.* 167(1): 275-284 (2005); Schmidt et al., *Development*, 134(16): 2913-23. (2007), US patent application US2007/0031437. Fitch et al. also describe a paralog of Egfl7 designated Egfl8 and indicate that its expression is similar to that of Egfl7, but that EGFL7 and EGFL8 may not overlap in function.

Despite the many advances in the field of angiogenesis, there remains a need to identify targets and develop means that can supplement or enhance the efficacy of existing anti-angiogenesis therapies.

SUMMARY OF THE INVENTION

The present invention is based, at least in part, on the discovery that EGF-like domain 8 (EGFL8) is involved in angiogenesis. Accordingly, the present invention provides novel compositions and uses thereof for inhibiting pathologic processes with an angiogenesis component.

In one aspect the invention provides a method of reducing or inhibiting angiogenesis in a subject having a pathological condition associated with angiogenesis, comprising administering to the subject an EGFL8 antagonist. In some embodiments, the EGFL8 antagonist is an anti-EGFL8 antibody. In some embodiments, the pathological condition is a neoplasm, e.g. a carcinoma. In some embodiments, the method further comprises administering a chemotherapeutic agent. In some embodiments, the pathological condition is associated with the eye. In some embodiments, the pathological condition is an intraocular neovascular disease.

In some embodiments, the method further comprises administering to the subject a second anti-angiogenic agent. In some embodiments, the second anti-angiogenic agent is administered prior to or subsequent to the administration of the EGFL8 antagonist. In some embodiments, the second anti-angiogenic agent is administered concurrently with the EGFL8 antagonist. In some embodiments, the second anti-angiogenic agent is an antagonist of EGFL7 or an antagonist of vascular endothelial cell growth factor (VEGF), e.g an anti-EGFL7 antibody or an anti-VEGF antibody (e.g. bevacizumab).

DETAILED DESCRIPTION OF THE PREFERRED EMBODIMENTS

Definitions

Figure 1A:
FIG. 1A and FIG. 1B show the expression pattern of Egfl7 and Egfl8 in E10.5 mouse embryonic cranial vasculatures.

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Spring Harbor Press (Cold Spring Harbor, N.Y. 1989). For purposes of the present invention, certain terms are defined below.

As used herein, the terms "EGFL8" and "EGFL8 polypeptide" refer to a polypeptide having the amino acid sequence of an EGFL8 polypeptide derived from nature, regardless of its mode of preparation or species. Thus, EGFL8 can have the amino acid sequence of naturally occurring human EGFL8, murine EGFL8, or EGFL8 from any other species. A full-length human EGFL8 amino acid sequence is:

(SEQ ID NO: 1)
MGSRAELCTLLGGFSFLLLLIPGEGAKGGSLRESQGVCSKQTLVVPLHYN

ESYSQPVYKPYLTLCAGRRICSTYRTMYRVMWREVRREVQQTHAVCCQGW

KKRHPGALTCEAICAKPCLNGGVCVRPDQCECAPGWGGKHCHVDVDECRT

SITLCSHHCFNTAGSFTCGCPHDLVLGVDGRTCMEGSPEPPTSASILSVA

VREAEKDERALKQEIHELRGRLERLEQWAGQAGAWVRAVLPVPPEELQPE

QVAELWGRGDRIESLSDQVLLLEERLGACSCEDNSLGLGVNHR.

A full-length murine EGFL8 amino acid sequence is:

(SEQ ID NO: 2)
MGLWAELCISLRGLSFFLVLMTGEGTRGGSFKESLGVCSKQTLLVPLRYN

ESYSQPVYKPYLTLCAGRRICSTYRTTYRVAWREVRREVPQTHVVCCQGW

KKPHPGALTCDAICSKPCLNGGVCTGPDRCECAPGWGGKHCHVDVDECRA

SLTLCSHGCLNTLGSFLCSCPHPLVLGLDGRTCAGGPPESPTSASILSVA

VREADSEEERALRWEVAELRGRLEKLEQWATQAGAWVRAVLPMPPEELRP

EQVAELWGRGDRIESLSDQVLLLEERLGACACEDNSLGPSLRG.

Such EGFL8 polypeptides can be isolated from nature or can be produced by recombinant and/or synthetic means.

"Isolated EGFL8" means EGFL8 that has been purified from an EGFL8 source or has been prepared by recombinant or synthetic methods and purified. Purified EGFL8 is substantially free of other polypeptides or peptides. "Substantially free" here means less than about 5%, preferably less than about 2%, more preferably less than about 1%, even more preferably less than about 0.5%, most preferably less than about 0.1% contamination with other source proteins.

The term "antagonist" is used in the broadest sense, and includes any molecule that partially or fully blocks, inhibits, or neutralizes a biological activity of EGFL8. Suitable antagonist molecules specifically include antagonist antibodies or antibody fragments, fragments or amino acid sequence variants of a native EGFL8 polypeptide, peptides, soluble fragments of EGFL8 receptor(s), antisense RNAs, ribozymes, RNAi, small organic molecules, etc. Methods for identifying antagonists of an EGFL8 polypeptide may comprise contacting an EGFL8 polypeptide with a candidate antagonist molecule and measuring a detectable change in one or more biological activities normally associated with the EGFL8 polypeptide.

"Active" or "activity" for the purposes herein refers to form(s) of EGFL8 which retain a biological and/or an immunological activity of EGFL8, wherein "biological" activity refers to a biological function (either inhibitory or stimulatory) caused by EGFL8 other than the ability to induce the production of an antibody against an antigenic epitope possessed by EGFL8 and an "immunological" activity refers to the ability to induce the production of an antibody against an antigenic epitope possessed by EGFL8. Principal biological activities of EGFL8 are its ability to promote vascular formation and to support endothelial cell adhesion and migration.

"EGFL8 receptor" is a molecule to which EGFL8 binds and which mediates a biological activity of EGFL8.

The term "antibody" herein is used in the broadest sense and specifically covers human, non-human (e.g. murine) and humanized monoclonal antibodies (including full length monoclonal antibodies), polyclonal antibodies, multispecific antibodies (e.g., bispecific antibodies), and antibody fragments so long as they exhibit the desired biological activity.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment that contains a complete antigen recognition and binding site. This region consists of a dimer of one heavy chain and one light chain variable domain in tight, non-covalent association.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise a portion of a full-length antibody, generally the antigen binding or variable domain thereof. Examples of antibody fragments include Fab, Fab', F(ab')$_2$, and Fv fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al. *Nature* 321:522-525 (1986); Reichmann et al. *Nature* 332:323-329 (1988); and Presta *Curr. Op. Struct. Biol.* 2:593-596 (1992).

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. Specifically, the treatment may directly prevent, slow down or otherwise decrease the pathology of cellular degeneration or damage, such as the pathology of tumor cells in cancer treatment, or may render the cells more susceptible to treatment by other therapeutic agents.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

A "chemotherapeutic agent" is a chemical compound useful in the treatment of cancer. Also included in this definition are anti-hormonal agents that act to regulate or inhibit hormone action on tumors such as anti-estrogens and selective estrogen receptor modulators (SERMs).

An "intraocular neovascular disease" is a disease characterized by ocular neovascularization. Examples of intraocular neovascular diseases include, but are not limited to, proliferative retinopathies including proliferative diabetic retinopathy, choroidal neovascularization (CNV), age-related macular degeneration (AMD), diabetic and other ischemia-related retinopathies, diabetic macular edema (DME), pathological myopia, von Hippel-Lindau disease, histoplasmosis of the eye, central retinal vein occlusion (CRVO), branched central retinal vein occlusion (BRVO), corneal neovascularization, retinal neovascularization, retinopathy of prematurity (ROP), subconjunctival hemorrhage, hypertensive retinopathy, etc.

The "pathology" of a disease includes all phenomena that compromise the well-being of the patient. For cancer, this includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "small molecule" is defined herein to have a molecular weight below about 500 Daltons.

Methods for Carrying Out the Invention

EGFL8

The human Egfl8 gene encodes a secreted protein of ~32 kD that is evolutionarily conserved. The human (*Homo sapiens*) amino acid sequence (SEQ ID NO: 1) shares about 80% homology to that of the mouse (*Mus musculus*; SEQ ID NO: 2). Accession numbers for EGFL8 polypeptides are: NM_030652 (*Homo sapiens*), NM_152922 (*Mus musculus*).

Preparation and Identification of Antagonists of EGFL8 Activity

Screening assays for antagonist drug candidates are designed to identify compounds that bind or complex with EGFL8 polypeptides, or otherwise interfere with the interaction of EGFL8 with other cellular proteins.

Small molecules may have the ability to act as EGFL8 antagonists and thus to be therapeutically useful. Such small molecules may include naturally occurring small molecules, synthetic organic or inorganic compounds and peptides. However, small molecules in the present invention are not limited to these forms. Extensive libraries of small molecules are commercially available and a wide variety of assays are well known in the art to screen these molecules for the desired activity.

In some embodiments, small molecule EGFL8 antagonists are identified by their ability to inhibit one or more of the biological activities of EGFL8. Thus a candidate compound is contacted with EGFL8. The biological activity of the EGFL8 is then assessed. In one embodiment the ability of EGFL8 to support endothelial cell adhesion and migration. A compound is identified as an antagonist where the biological activity of EGFL8 is inhibited.

Compounds identified as EGFL8 antagonists may be used in the methods of the present invention. For example, EGFL8 antagonists may be used to treat cancer.

For cancer, a variety of well-known animal models can be used to further understand the role of EGFL8 in the development and pathogenesis of tumors, and to test the efficacy of candidate therapeutic agents, including antibodies and other antagonists of native EGFL8 polypeptides, such as small-molecule antagonists. The in vivo nature of such models makes them particularly predictive of responses in human patients. Animal models of tumors and cancers (e.g., breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngeneic mice using standard techniques, e.g., subcutaneous injection, tail vein injection, spleen implantation, intraperitoneal implantation, implantation under the renal capsule, or orthopin implantation, e.g., colon cancer cells implanted in colonic tissue. See, e.g., PCT publication No. WO 97/33551, published Sep. 18, 1997. Probably the most often used animal species in oncological studies are immunodeficient mice and, in particular, nude mice. The observation that the nude mouse with thymic hypo/aplasia could successfully act as a host for human tumor xenografts has lead to its widespread use for this purpose. The autosomal recessive nu gene has been introduced into a very large number of distinct congenic strains of nude mouse, including, for example, ASW, A/He, AKR, BALB/c, B10.LP, C17, C3H, C57BL, C57, CBA, DBA, DDD, I/st, NC, NFR, NFS, NFS/N, NZB, NZC, NZW, P, RIII, and SJL. In addition, a wide variety of other animals with inherited immunological defects other than the nude mouse have been bred and used as recipients of tumor xenografts. For further details see, e.g., *The Nude Mouse in Oncology Research*, E. Boven and B. Winograd, eds. (CRC Press, Inc., 1991).

The cells introduced into such animals can be derived from known tumor/cancer cell lines, such as any of the above-listed tumor cell lines, and, for example, the B104-1-1 cell line (stable NIH-3T3 cell line transfected with the neu protooncogene); ras-transfected NIH-3T3 cells; Caco-2 (ATCC® HTB-37); or a moderately well-differentiated grade II human colon adenocarcinoma cell line, HT-29 (ATCC® HTB-38); or from tumors and cancers. Samples of tumor or cancer cells can be obtained from patients undergoing surgery, using standard conditions involving freezing and storing in liquid nitrogen. Karmali et al., *Br. J. Cancer* 48:689-696 (1983).

Tumor cells can be introduced into animals, such as nude mice or EGFL8 knockout mice, by a variety of procedures. The subcutaneous (s.c.) space in mice is very suitable for tumor implantation. Tumors can be transplanted s.c. as solid blocks, as needle biopsies by use of a trochar, or as cell suspensions. For solid-block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue.

Animal models of breast cancer can be generated, for example, by implanting rat neuroblastoma cells (from which the neu oncogene was initially isolated), or neu-transformed NIH-3T3 cells into nude mice, essentially as described by Drebin et al. *Proc. Nat. Acad. Sci. USA* 83:9129-9133 (1986).

Similarly, animal models of colon cancer can be generated by passaging colon cancer cells in animals, e.g., nude mice, leading to the appearance of tumors in these animals. An orthotopic transplant model of human colon cancer in nude mice has been described, for example, by Wang et al., *Cancer Research* 54:4726-4728 (1994) and Too et al., *Cancer Research* 55:681-684 (1995). This model is based on the so-called "METAMOUSE®" sold by AntiCancer, Inc., (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A, CMS4, CMS5, CMS21, and WEHI-164 are chemically induced fibrosarcomas of BALB/c female mice (DeLeo et al., *J. Exp. Med.* 146:720 (1977)), which provide a highly controllable model system for studying the anti-tumor activities of various agents. Palladino et al., *J. Immunol.* 138:4023-4032 (1987). Briefly, tumor cells are propagated in vitro in cell culture. Prior to injection into the animals, the cell lines are washed and suspended in buffer, at a cell density of about $10\times10^6$ to $10\times10^7$ cells/ml. The animals are then infected subcutaneously with 10 to 100 µl of the cell suspension, allowing one to three weeks for a tumor to appear.

In addition, the Lewis lung carcinoma of mice, which is one of the most thoroughly studied experimental tumors, can be used as an investigational tumor model. Efficacy in this tumor model has been correlated with beneficial effects in the treatment of human patients diagnosed with small-cell carcinoma of the lung (SCCL). This tumor can be introduced in normal mice upon injection of tumor fragments from an affected mouse or of cells maintained in culture. Zupi et al., *Br. J. Cancer* 41:suppl. 4, 30 (1980). Evidence indicates that tumors can be started from injection of even a single cell and that a very high proportion of infected tumor cells survive. For further information about this tumor model see, Zacharski, *Haemostasis* 16:300-320 (1986).

One way of evaluating the efficacy of a test compound in an animal model with an implanted tumor is to measure the size of the tumor before and after treatment. Traditionally, the size of implanted tumors has been measured with a slide caliper in two or three dimensions. The measure limited to two dimensions does not accurately reflect the size of the tumor; therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, *Proc. 6th Int. Workshop on Immune-Deficient Animals*, Wu and Sheng eds. (Basel, 1989), p. 301. It is noted, however, that necrosis and inflammatory responses following treatment may actually result in an increase in tumor size, at least initially. Therefore, these changes need to be carefully monitored, by a combination of a morphometric method and flow cytometric analysis.

The efficacy of antibodies specifically binding EGFL8 identified herein, and other drug candidates, can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor. These tumors are usually not amenable to surgery, primarily because of the anatomy of the feline oral cavity. At present, there is no effective treatment for this tumor. Prior to entry into the study, each cat undergoes complete clinical examination and biopsy, and is scanned by computed tomography (CT). Cats diagnosed with sublingual oral squamous cell tumors are excluded from the study. The tongue can become paralyzed as a result of such tumor, and even if the treatment kills the tumor, the animals may not be able to feed themselves. Each cat is treated repeatedly, over a longer period of time. Photographs of the tumors will be taken daily during the treatment period, and at each subsequent recheck. After treatment, each cat undergoes another CT scan. CT scans and thoracic radiograms are evaluated every 8 weeks thereafter. The data are evaluated for differences in survival, response, and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chondroma, or leiomyosarcoma of dogs, cats, and baboons can also be tested. Of these, mammary adenocarcinoma in dogs and cats is a preferred model as its appearance and behavior are very similar to those in humans. However, the use of this model is limited by the rare occurrence of this type of tumor in animals.

Other in vitro and in vivo cardiovascular, endothelial, and angiogenic tests known in the art are also suitable herein.

Antibody Binding Studies

The ability of anti-EGFL8 antibodies to inhibit the effect of EGFL8 on endothelial cells or other cells used in the cardiovascular, endothelial, and angiogenic assays is tested. Exemplary antibodies include polyclonal, monoclonal, humanized, bispecific, and heteroconjugate antibodies, the preparation of which is described herein.

Antibody binding studies may be carried out in any known assay method, such as competitive binding assays, direct and indirect sandwich assays, and immunoprecipitation assays. Zola, *Monoclonal Antibodies: A Manual of Techniques* (CRC Press, Inc., 1987), pp. 147-158.

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte that remain unbound.

Sandwich assays involve the use of two antibodies, each capable of binding to a different immunogenic portion, or epitope, of the protein to be detected. In a sandwich assay, the test sample analyte is bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

The compositions useful in the treatment of cardiovascular, endothelial, and angiogenic disorders include, without limitation, antibodies, small organic and inorganic molecules, peptides, phosphopeptides, antisense, siRNA and ribozyme molecules, triple-helix molecules, etc., that inhibit the expression and/or activity of the target gene product.

More specific examples of potential antagonists include an oligonucleotide that binds to EGFL8, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of EGFL8 that recognizes the receptor but imparts no effect, thereby competitively inhibiting the action of EGFL8.

Another potential EGFL8 antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature EGFL8 polypeptides herein, is used to design an antisense RNA oligonucleotide of from about 10 to 40 base pairs in length. A DNA oligonucleotide is designed to be complementary to a region of the gene involved in transcription (triple helix—see, Lee et al., *Nucl. Acids Res.* 6:3073 (1979); Cooney et al., *Science* 241:456 (1988); Dervan et al., *Science* 251:1360 (1991)), thereby preventing transcription and the production of EGFL8. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex helix formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex. The antisense RNA oligonucleotide hybridizes to the mRNA in vivo and blocks translation of the mRNA molecule into EGFL8 (antisense—Okano, *Neurochem.* 56:560 (1991); *Oligodeoxynucleotides as Antisense Inhibitors of Gene Expression* (CRC Press: Boca Raton, Fla., 1988).

The antisense oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., *Proc. Natl. Acad. Sci. U.S.A.* 86:6553-6556 (1989); Lemaitre, et al., *Proc. Natl. Acad. Sci. U.S.A.* 84:648-652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., *BioTechniques* 6:958-976 (1988)) or intercalating agents (see, e.g., Zon, *Pharm. Res.* 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an anomeric oligonucleotide. An anomeric oligonucleotide forms specific double-stranded hybrids with complementary RNA in which, contrary to the usual units, the strands run parallel to each other (Gautier, et al., *Nucl. Acids Res.* 15:6625-6641 (1987)). The oligonucleotide is a 2'-0-methylribonucleotide (Inoue, et al., *Nucl. Acids Res.* 15:6131-6148 (1987)), or a chimeric RNA-DNA analogue (Inoue, et al., *FEBS Lett.* 215:327-330 (1987)).

In some embodiments, the antagonists are inhibitory duplex RNAs, e.g. siRNA, shRNA, etc.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (*Nucl. Acids Res.* 16:3209 (1988)), methylphosphonate oligonucleotides can be prepared by use of controlled pore glass polymer supports (Sarin, et al., *Proc. Natl. Acad. Sci. U.S.A.* 85:7448-7451 (1988)), etc.

The oligonucleotides described above can also be delivered to cells such that the antisense RNA or DNA may be expressed in vivo to inhibit production of EGFL8. When antisense DNA is used, oligodeoxyribonucleotides derived from the translation-initiation site, e.g., between about −10 and +10 positions of the target gene nucleotide sequence, are preferred.

Potential antagonists further include small molecules that bind to EGFL8, thereby blocking its activity. Examples of small molecules include, but are not limited to, small peptides or peptide-like molecules, preferably soluble peptides, and synthetic non-peptidyl organic or inorganic compounds.

Additional potential antagonists are ribozymes, which are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology* 4:469-471 (1994), and PCT publication No. WO 97/33551 (published Sep. 18, 1997).

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions which form complementary base pairs with the target mRNA. The sole requirement is that the target mRNA have the following sequence of two bases: 5'-UG-3'. The construction and production of hammerhead ribozymes is well known in the art and is described more fully in Myers, *Molecular Biology and Biotechnology: A Comprehensive Desk Reference*, VCH Publishers, New York (1995), (see especially FIG. 4, page 833) and in Haseloff and Gerlach, *Nature,* 334:585-591 (1988), which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophile* (known as the IVS, or L-19 IVS RNA) and which has been extensively described by Thomas Cech and collaborators (Zaug, et al., *Science,* 224:574-578 (1984); Zaug and Cech, *Science,* 231:470-475 (1986); Zaug, et al., *Nature,* 324:429-433 (1986); published International patent application No. WO 88/04300 by University Patents Inc.; Been and Cech, *Cell,* 47:207-216 (1986)). The Cech-type ribozymes have an eight base pair active site that hybridizes to a target RNA sequence whereafter cleavage of the target RNA takes place. The invention encompasses those Cech-type ribozymes that target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes, unlike antisense molecules, are catalytic, a lower intracellular concentration is required for efficiency.

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

Another use for EGFL8 antagonists is in the prevention of tumor angiogenesis, which involves vascularization of a tumor to enable it to growth and/or metastasize. This process is dependent on the growth of new blood vessels. Examples of neoplasms and related conditions that involve tumor angiogenesis include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The EGFL8 antagonists can also be useful in treating intraocular neovascular diseases including, but are not limited to, proliferative retinopathies including proliferative diabetic retinopathy, choroidal neovascularization (CNV), age-related macular degeneration (AMD), diabetic and other ischemia-related retinopathies, diabetic macular edema (DME), pathological myopia, von Hippel-Lindau disease, histoplasmosis of the eye, central retinal vein occlusion (CRVO), branched central retinal vein occlusion (BRVO), corneal neovascularization, retinal neovascularization, retinopathy of prematurity (ROP), subconjunctival hemorrhage, hypertensive retinopathy, etc.

Rheumatoid arthritis is a further indication. Blood vessel growth and targeting of inflammatory cells through the vasculature is an important component in the pathogenesis of rheumatoid and sero-negative forms of arthritis.

In view of the above, EGFL8, antagonists thereof described herein, which are shown to alter or impact endothelial cell function and migration, are likely to play an important role in the etiology and pathogenesis of many or all of the disorders noted above, and as such can serve as therapeutic targets to inhibit these processes or for vascular-related drug targeting in these disorders.

Administration Protocols, Schedules, Doses, and Formulations

The EGFL8 antagonists are pharmaceutically useful as a prophylactic and therapeutic agent for various disorders and diseases as set forth above.

Therapeutic compositions of EGFL8 antagonists are prepared for storage by mixing the desired molecule having the appropriate degree of purity with optional pharmaceutically acceptable carriers, excipients, or stabilizers (Remington's Pharmaceutical Sciences, 16th edition, Osol, A. ed. (1980)), in the form of lyophilized formulations or aqueous solutions.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Additional examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of antagonist include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. EGFL8 antagonists will typically be formulated in such vehicles at a concentration of about 0.1 mg/ml to 100 mg/ml.

Another formulation comprises incorporating EGFL8 antagonist into formed articles. Such articles can be used in modulating endothelial cell growth and angiogenesis. In addition, tumor invasion and metastasis may be modulated with these articles.

EGFL8 antagonists to be used for in vivo administration must be sterile. This is readily accomplished by filtration through sterile filtration membranes, prior to or following lyophilization and reconstitution. If in lyophilized form, EGFL8 antagonist is typically formulated in combination with other ingredients for reconstitution with an appropriate diluent at the time for use. An example of a liquid formulation of EGFL8 antagonist is a sterile, clear, colorless unpreserved solution filled in a single-dose vial for subcutaneous injection. Preserved pharmaceutical compositions suitable for repeated use may contain, for example, depending mainly on the indication and type of polypeptide:
  EGFL8 antagonist;
  a buffer capable of maintaining the pH in a range of maximum stability of the polypeptide or other molecule in solution, preferably about 4-8;
  a detergent/surfactant primarily to stabilize the polypeptide or molecule against agitation-induced aggregation;
  an isotonifier;
  a preservative selected from the group of phenol, benzyl alcohol and a benzethonium halide, e.g., chloride; and
  water.

If the detergent employed is non-ionic, it may, for example, be polysorbates (e.g., POLYSORBATE™ (TWEEN™) 20, 80, etc.) or poloxamers (e.g., POLOXAMER™188). The use of non-ionic surfactants permits the formulation to be exposed to shear surface stresses without causing denaturation of the polypeptide. Further, such surfactant-containing formulations may be employed in aerosol devices such as those used in a pulmonary dosing, and needleless jet injector guns (see, e.g., EP 257,956).

An isotonifier may be present to ensure isotonicity of a liquid composition of EGFL8 antagonist, and includes polyhydric sugar alcohols, preferably trihydric or higher sugar alcohols, such as glycerin, erythritol, arabitol, xylitol, sorbitol, and mannitol. These sugar alcohols can be used alone or in combination. Alternatively, sodium chloride or other appropriate inorganic salts may be used to render the solutions isotonic.

The buffer may, for example, be an acetate, citrate, succinate, or phosphate buffer depending on the pH desired. The pH of one type of liquid formulation of this invention is buffered in the range of about 4 to 8, preferably about physiological pH.

The preservatives phenol, benzyl alcohol and benzethonium halides, e.g., chloride, are known antimicrobial agents that may be employed.

Therapeutic polypeptide compositions described herein generally are placed into a container having a sterile access port, for example, an intravenous solution bag or vial having a stopper pierceable by a hypodermic injection needle. The formulations are preferably administered as repeated intravenous (i.v.), subcutaneous (s.c.), or intramuscular (i.m.) injections, or as aerosol formulations suitable for intranasal or intrapulmonary delivery (for intrapulmonary delivery see, e.g., EP 257,956).

Therapeutic polypeptides can also be administered in the form of sustained-released preparations. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15:167-277 (1981) and Langer, *Chem. Tech.* 12:98-105 (1982) or poly(vinylalcohol)), polylactides (U.S. Pat. No. 3,773,919, EP 58,481), copolymers of L-glutamic acid and gamma ethyl-L-glutamate (Sidman et al., *Biopolymers* 22:547-556 (1983)), non-degradable ethylene-vinyl acetate (Langer et al., supra), degradable lactic acid-glycolic acid copolymers such as the Lupron Depot® (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release EGFL8 antagonist compositions also include liposomally entrapped antagonists. Such liposomes are prepared by methods known per se: DE 3,218,121; Epstein et al., *Proc. Natl. Acad. Sci. USA* 82:3688-3692 (1985); Hwang et al., *Proc. Natl. Acad. Sci. USA* 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal therapy.

The therapeutically effective dose of EGFL8 antagonist will, of course, vary depending on such factors as the pathological condition to be treated (including prevention), the method of administration, the type of compound being used for treatment, any co-therapy involved, the patient's age, weight, general medical condition, medical history, etc., and its determination is well within the skill of a practicing physician. Accordingly, it will be necessary for the therapist to titer the dosage and modify the route of administration as required to obtain the maximal therapeutic effect.

With the above guidelines, the effective dose generally is within the range of from about 0.001 to about 1.0 mg/kg, more preferably about 0.01-1.0 mg/kg, most preferably about 0.01-0.1 mg/kg.

The route of EGFL8 antagonist administration is in accord with known methods, e.g., by injection or infusion by intravenous, intramuscular, intracerebral, intraperitoneal, intracerobrospinal, subcutaneous, intraocular, intraarticular, intrasynovial, intrathecal, oral, topical, or inhalation routes, or by sustained-release systems as noted below. EGFL8 antagonists also are suitably administered by intratumoral, peritumoral, intralesional, or perilesional routes, to exert local as well as systemic therapeutic effects. The intraperitoneal route is expected to be particularly useful, for example, in the treatment of ovarian tumors.

If a peptide or small molecule is employed as an antagonist, it is preferably administered orally or non-orally in the form of a liquid or solid to mammals.

Examples of pharmacologically acceptable salts of molecules that form salts and are useful hereunder include alkali metal salts (e.g., sodium salt, potassium salt), alkaline earth metal salts (e.g., calcium salt, magnesium salt), ammonium salts, organic base salts (e.g., pyridine salt, triethylamine salt), inorganic acid salts (e.g., hydrochloride, sulfate, nitrate), and salts of organic acid (e.g., acetate, oxalate, p-toluenesulfonate).

Combination Therapies

The effectiveness of EGFL8 antagonist in preventing or treating the disorder in question may be improved by administering the active agent serially or in combination with another agent that is effective for those purposes, either in the same composition or as separate compositions.

For example, EGFL8 antagonists used to treat angiogenesis associated conditions such as cancer or ocular diseases may be combined with cytotoxic, chemotherapeutic, or anti-angiogenic agents as identified above. It is desirable to use EGFL8 antagonists in combination with another anti-angiogenic agent. In some embodiments, the EGFL8 antagonist is used in combination with a VEGF antagonist, e.g. an antibody, e.g. bevacizumab. In some embodiments, the EGFL8 antagonist is used in combination with an EGFL7 antagonist.

The effective amounts of the therapeutic agents administered in combination with EGFL8 antagonist will be at the physician's or veterinarian's discretion. Dosage administration and adjustment is done to achieve maximal management of the conditions to be treated. For example, for treating hypertension, these amounts ideally take into account use of diuretics or digitalis, and conditions such as hyper- or hypotension, renal impairment, etc. The dose will additionally depend on such factors as the type of the therapeutic agent to be used and the specific patient being treated. Typically, the amount employed will be the same dose as that used, if the given therapeutic agent is administered without EGFL8.

EGFL8 Antibodies

Some of the most promising drug candidates according to the present invention are antibodies and antibody fragments that may inhibit the production of EGFL8 and/or reduce the activity of EGFL8.

Polyclonal Antibodies

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the EGFL8 polypeptide or a fusion protein thereof. It may be useful to conjugate the immunizing agent to a protein known to be immunogenic in the mammal being immunized. Examples of such immunogenic proteins include, but are not limited to, keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A or synthetic trehalose dicorynomycolate). The immunization protocol may be selected by one skilled in the art without undue experimentation.

Monoclonal Antibodies

The anti-EGFL8 antibodies may, alternatively, be monoclonal antibodies. Monoclonal antibodies may be prepared using hybridoma methods, such as those described by Kohler and Milstein, *Nature* 256:495 (1975). In a hybridoma method, a mouse, hamster, or other appropriate host animal is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the EGFL8 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice* (New York: Academic Press, 1986), pp. 59-103. Immortalized cell lines are usually transformed mammalian cells, particularly myeloma cells of rodent, bovine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J. Immunol.* 133:3001 (1984); Brodeur et al., *Monoclonal Antibody Production Techniques and Applications* (Marcel Dekker, Inc.: New York, 1987) pp. 51-63.

The culture medium in which the hybridoma cells are cultured can then be assayed for the presence of monoclonal antibodies directed against the EGFL8 polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.* 107:220 (1980).

After the desired hybridoma cells are identified, the clones may be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy- and light-chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking In vitro methods are also suitable for preparing monovalent antibodies. Digestion of antibodies to produce fragments thereof, particularly Fab fragments, can be accomplished using routine techniques known in the art.

Human and Humanized Antibodies

The anti-EGFL8 antibodies may further comprise humanized antibodies or human antibodies. Humanized forms of non-human (e.g., murine) antibodies are chimeric immunoglobulins, immunoglobulin chains, or fragments thereof (such as Fv, Fab, Fab', F(ab')$_2$, or other antigen-binding subsequences of antibodies) that contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody preferably also will comprise at least a portion of an immunoglobulin constant region (Fc), typically that of a human immunoglobulin. Jones et al., *Nature* 321:522-525 (1986); Riechmann et al., *Nature* 332:323-329 (1988); Presta, *Curr. Op. Struct. Biol.* 2:593-596 (1992).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries. Hoogenboom and Winter, *J. Mol. Biol.* 227:381 (1991); Marks et al., *J. Mol. Biol.* 222:581 (1991). The techniques of Cole et al. and Boerner et al. are also available for the preparation of human monoclonal antibodies. Cole et al., *Monoclonal Antibodies and Cancer Therapy*, Alan R. Liss, p. 77 (1985) and Boerner et al., *J. Immunol.* 147(1):86-95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; and 5,661,016, and in the following scientific publications: Marks et al., *Bio/Technology* 10:779-783 (1992); Lonberg et al., *Nature* 368:856-859 (1994); Morrison, *Nature,* 368:812-813 (1994); Fishwild et al., *Nature Biotechnology* 14:845-851 (1996); Neuberger, *Nature Biotechnology* 14:826 (1996); Lonberg and Huszar, *Intern. Rev. Immunol.* 13:65-93 (1995).

Bispecific Antibodies

Bispecific antibodies are monoclonal, preferably human or humanized, antibodies that have binding specificities for at least two different antigens. In the present case, one of the binding specificities is for the EGFL8 polypeptide, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities. Milstein and Cuello, *Nature* 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.* 10:3655-3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., *Methods in Enzymology* 121:210 (1986).

Heteroconjugate Antibodies

Heteroconjugate antibodies are composed of two covalently joined antibodies. Such antibodies have, for example, been proposed to target immune-system cells to unwanted cells (U.S. Pat. No. 4,676,980), and for treatment of HIV infection. WO 91/00360; WO 92/200373; EP 03089. It is contemplated that the antibodies may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triamine-pentaacetic acid (MX-DTPA) is an exemplary chelating agent for conjugation of radionucleotide to the antibody. See, WO94/11026.

In another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Immunoliposomes

The antibodies disclosed herein may also be formulated as immunoliposomes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257:286-288 (1982) via a disulfide-interchange reaction. A chemotherapeutic agent (such as Doxorubicin) is optionally contained within the liposome. See, Gabizon et al., *J. National Cancer Inst.* 81(19):1484 (1989).

Pharmaceutical Compositions of Antibodies

Antibodies specifically binding an EGFL8 polypeptide identified herein, as well as other molecules identified by the screening assays disclosed hereinbefore, can be administered for the treatment of various disorders as noted above and below in the form of pharmaceutical compositions.

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Methods of Treatment Using the Antibody

It is contemplated that the antibodies to an EGFL8 polypeptide may be used to treat various angiogenesis associated conditions as noted above.

The antibodies are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

Other therapeutic regimens may be combined with the administration of the antibodies of the instant invention as noted above. For example, if the antibodies are to treat cancer, the patient to be treated with such antibodies may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in *Chemotherapy Service*, Ed., M. C. Perry (Williams & Wilkins: Baltimore, Md., 1992). The chemotherapeutic agent may precede, or follow administration of the antibody, or may be given simultaneously therewith.

If the antibodies are used for treating cancer, it may be desirable also to administer antibodies against other tumor-associated antigens, such as antibodies that bind to one or more of the ErbB2, EGFR, ErbB3, ErbB4, or VEGF receptor(s). These also include the agents set forth above. Also, the antibody is suitably administered serially or in combination with radiological treatments, whether involving irradiation or administration of radioactive substances. Alternatively, or in addition, two or more antibodies binding the same or two or more different antigens disclosed herein may be co-administered to the patient. Sometimes, it may be beneficial also to administer one or more cytokines to the patient. In a preferred embodiment, the antibodies herein are co-administered with a growth-inhibitory agent. For example, the growth-inhibitory agent may be administered first, followed by an antibody of the present invention. However, simultaneous administration or administration of the antibody of the present invention first is also contemplated. Suitable dosages for the growth-inhibitory agent are those presently used and may be lowered due to the combined action (synergy) of the growth-inhibitory agent and the antibody herein.

In one embodiment, vascularization of tumors is attacked in combination therapy. The anti-EGFL8 antibody and another antibody (e.g., anti-VEGF) are administered to tumor-bearing patients at therapeutically effective doses as determined, for example, by observing necrosis of the tumor or its metastatic foci, if any. Additional anti-tumor agents can be further administered, such as alpha-, beta-, or gamma-interferon, anti-HER2 antibody, heregulin, anti-heregulin antibody, D-factor, interleukin-1 (IL-1), interleukin-2 (IL-2), granulocyte-macrophage colony stimulating factor (GM-CSF), or agents that promote microvascular coagulation in tumors, such as anti-protein C antibody, anti-protein S antibody, or C4b binding protein (see, WO 91/01753, published 21 Feb. 1991), or heat or radiation.

In other embodiments, a FGF or PDGF antagonist, such as an anti-FGF or an anti-PDGF neutralizing antibody, is administered to the patient in conjunction with the anti-EGFL8 antibody. Treatment with anti-EGFL8 antibodies preferably may be suspended during periods of wound healing or desirable neovascularization.

For the prevention or treatment of cardiovascular, endothelial, and angiogenic disorder, the appropriate dosage of an antibody herein will depend on the type of disorder to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

For example, depending on the type and severity of the disorder, about 1 μg/kg to 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 μg/kg to 100 mg/kg or more, depending on the factors mentioned above. For repeated administrations over several days or longer, depending on the condition, the treatment is repeated or sustained until a desired suppression of disorder symptoms occurs. However, other dosage regimens may be useful. The progress of this therapy is easily monitored by conventional techniques and assays, including, for example, radiographic tumor imaging.

The following Examples are offered for illustrative purposes only, and are not intended to limit the scope of the present invention in any way.

The disclosures of all patent and literature references cited in the present specification are hereby incorporated by reference in their entirety.

EXAMPLES

Commercially available reagents referred to in the Examples were used according to manufacturer's instructions unless otherwise indicated. The source of those cells identified herein by ATCC® accession numbers is the American Type Culture Collection, Manassas, Va. 20108.

All references cited herein are hereby incorporated by reference.

Example 1

Egfl8 is Expressed in the Vasculature

We performed experiments to determine the expression pattern of Egfl8 and, in particular, to compare its expression with that of Egfl7. The antisense riboprobes for in situ hybridizations were as follows:

For Egfl7:

```
                                         (SEQ ID NO: 3)
GTAGGGCTCTGCCGGGACCTGGGTCTTCCCTCTCCTGGAGCTGCAGAGGC

CAGAAGTTCAGTGGTGAGGGGTCCAAGGAGAGTCCGGGGAGACCAGGGAG

GCTCTGTCCATCCCCTGTCCCTGTCCCTGTGGGAAGCCCCCGGCAGCAGC

AAGACGCTGGCTGTTCCACCTGCCCACAAGAACAGCCACCACCAGTACCC

AGGGGATGACAAGCGGCCGGACCACAGGCCACAAAAAGAAGAAGGCTACC

CCACTTACAGATGCAGACCATGTGGGGCTCCGGAGAACTGCTTGTAGCAT

GGTTTCTAGTGTTGGCAGCAGATGGTACTACTGAGCATGTCTACAGACCC

AGCCGTAGAGTGTGTACTGTGGGGATTTCCGGAGGTTCCATCTCGGAGAC

CTTTGTGCAGCGTGTATACCAGCCTTACCTCACCACTTGCGACGGACACA

GAGCCTGCAGCACCTACCGAACCATCTACCGGACTGCCTATCGCCGTAGC

CCTGGGGTGACTCCCGCAAGGCCTCGCTATGCTTGCTGCCCTGGTTGGAA

GAGGACCAGTGGGCTCCCTGGGGCTTGTGGAGCAGCAATATGCCAGCCTC

CATGTGGGAATGGAGGGAGTTGCATCCGCCCAGGACACTGCCGCTGCCCT

GTGGGATGGCAGGGAGATACTTGCCAGACAGATGTTGATGAATGCAGTAC

AGGAGAGGCCAGTTGTCCCCAGCGCTGTGTCAATACTGTGGGAAGTTACT

GGTGCCAGGGATGGGAGGGACAAAGCCCATCTGCAGATGGGACGCGCTGC

CTGTCTAAGGAGGGGCCCTCCCCGGTGGCCCCAAACCCCACAGCAGGAGT

GGACAGCATGGCGAGAGAGGAGGTGTACAGGCTGCAGGCTCGGGTTGATG

TGCTAGAACAGAAACTGCAGTTGGTGCTGGCCCCACTGCACAGCCTGGCC

TCTCGGTCCACAGAGCATGGGCTACAAGATCCTGGCAGCCTGCTGGCCCA

TTCCTTCCAGCAGCTGGACCGAATTGATTCACTGAGTGAGCAGGTGTCCT

TCTTGGAGGAACATCTGGGGTCCTGCTCCTGCAAAAAAGATCTGTGATAA

CCTCTCACCACCCAGGCTGGATAGAGCAGTCATCCCTAGATCCCTTGTAG

CCAGAGTTCAGGCGCTGTCTGGTGGTGCCTATGAGCAGAAGGCCCTGCCT

CATTGTCCCTCTTTCTTAGGAGGTTCCTAGGACTTGGGCATGGGGAGTGG

GGTCTTGTGTGACTCTTCAGTGGGGCTCCCTGTCTAAGTGGTAAGGTGGG

GATTGTCTCCATCTTTGTCATAATAAAGCTGAGACTT
```

For Egfl8:

```
                                         (SEQ ID NO: 4)
GGAGGATCTTTCAAAGAGAGTTTGGGAGTGTGCTCCAAGCAGACGCTGCT

GGTTCCTCTCCGTTACAACGAGTCCTATAGTCAACCGGTGTACAAACCCT

ACCTGACCTTGTGTGCGGGGAGGCGCATATGTAGCACCTACAGGACCACA

TACCGTGTGGCCTGGCGGGAGGTGAGGCGGGAGGTACCACAGACACACGT

GGTGTGCTGTCAGGGCTGGAAGAAGCCACACCCAGGAGCTCTCACCTGTG

ATGCCATCTGCTCCAAGCCTTGTCTTAATGGAGGTGTCTGCACTGGACCA

GACCGGTGCGAGTGTGCCCCAGGCTGGGGAGGAAAGCATTGCCACGTGGA

TGTCGATGAATGCAGGGCCAGCCTTACCCTCTGCTCTCATGGCTGCCTCA

ACACACTGGGCAGCTTCTTGTGCAGCTGTCCACACCCCCTGGTGCTGGGT

CTCGATGGACGCACCTGTGCAGGAGGCCCACCGGAGAGTCCAACCAGCGC

G.
```

Mouse embryos were dissected out of the uterus and washed in PBS (RNase free). E10.5 CD1 mouse embryos were fixed in freshly prepared 4% paraformaldehyde in PBS for 4 hours at room temperature (RT), washed 2×5 min with PBT (PBS+0.1% Tween™ 20), and dehydrated on ice through 25%, 50%, 75%, 2×100% methanol in PBT each for 5-10 min. Embryos were bleached at RT in methanol/$H_2O_2$ (4:1) for 1 hour, washed 2×10 min with 100% methanol on ice and stored in 100% Methanol at −20° C. until ready for hybridization.

Embryos were incubated in the following buffers sequentially: 75%, 50%, 25% methanol in PBT each for 5-10 min on ice. Embryos were washed 3×5 min in PBT on ice, then for 30 min in 20 µg/ml proteinase K in PBT at RT with gentle rocking, rinsed twice carefully with cold PBT, fixed for 20 min with 0.2% glutaraldehyde+4% PFA in PBS at RT with gentle rocking, washed 3×5 min in PBT at RT. They were then incubated for 5 min in 50% PBT+50% Prehybridization Mix (25 ml ultrapure deionized formamide; 12.5 ml 20×SSC (5× final); 40 µl 50 mg/ml Heparin; 500 µl 10 mg/ml salmon sperm DNA; 125 µl 20 mg/ml yeast tRNA; 500 µl 10% Tween™ 20; ~2-4 ml 1 M Citric Acid Anhydrous until pH=4.5-5; RNase free water to 50 ml), then 5 min in Prehybridization Mix. The solution was removed and then they were prehybridized for 3-6 hours in Prehybridization Mix at 68-70° C. with rocking and then hybridized overnight at 70° C. with shaking in: 2 ml Prehybridization Mix with 50 µl Formamide and 1 µg/ml dig-riboprobe (denature riboprobe for 5-10 min at 80° C. before adding to the hybridization mixture).

After hybridization, embryos were washed multiple times: rinsed twice with prewarmed solution I (125 ml Formamide; 62.5 ml 20×SSC (final 5×); 2.5 ml 10% Tween™ 20; water to 250 ml) at 68-70° C.; then 2×30 min prewarmed solution I at 68-70° C. with rocking; then 3×60 min solution II (125 ml Formamide; 25 ml 20×SSC (final 2×); 2.5 ml 10% Tween™ 20; water to 250 ml) at 68-70° C. with rocking; 3×5 min with TBST (8 g NaCl; 0.2 g KCl; 2.5 ml 1 M Tris pH7.4 or 7.5; 10 ml 10% Tween™ 20; Add water to 1 liter) at RT with rocking; and then 60 min TBST/10% heat inactivated sheep (or lamb) serum at RT with rocking. Diluted ½₀₀₀ sheep anti-Dig antibody (from Roche Molecular Diagnostics) in TBST/1% heat inactivated sheep serum was then added and incubated overnight at 4° C. with rocking.

The embryos were then washed 3×5 min TBST at RT with rocking, washed all day at RT with rocking, change TBST every hour, and then washed in TBST at 4° C. overnight with rocking. They were then washed 2×20 min in freshly prepared AP buffer (2 ml 5M NaCl, 0.2 g KCl, 2.5 ml 1 M Tris pH7.4 or 7.5, 10 ml 10% Tween™ 20, water to 100 ml) at RT with rocking. The color was then developed by adding 10 ml AP buffer+200 μl NBT/BCIP solution, wrapping the tubes in foil and rocking. The reaction was stopped with 3 washes of PBT/1 mM EDTA, the embryos were postfixed with 4% PFA in PBS for 20 min at RT, washed a few times with PBT and stored embryos in: 80% Glycerol in PBS+0.1% $NaN_3$ at 4° C.

Figure 1B:
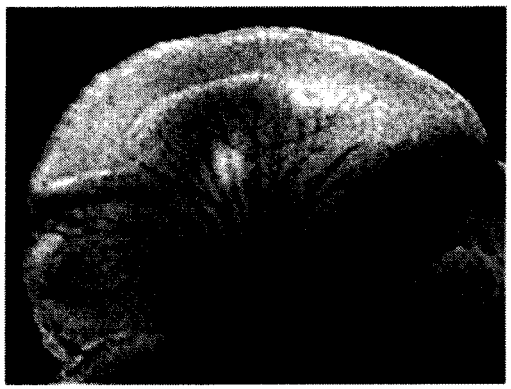

We observed that while Egfl7 was expressed in the majority of cranial vessels including arteries and veins, whereas only a subset of cranial arteries expressed Egfl8 (FIG. 1A and FIG. 1B). Specifically, Egfl8 appears to be restricted in certain segments of the arterial branching hierarchy. In addition, we perform similar experiments using in vivo mouse tumor models and observe that Egfl8 is expressed in certain vessels in tumors.

Example 2

Egfl8 Knockout Mice Exhibit Defects in Angiogenesis

Figure 2:
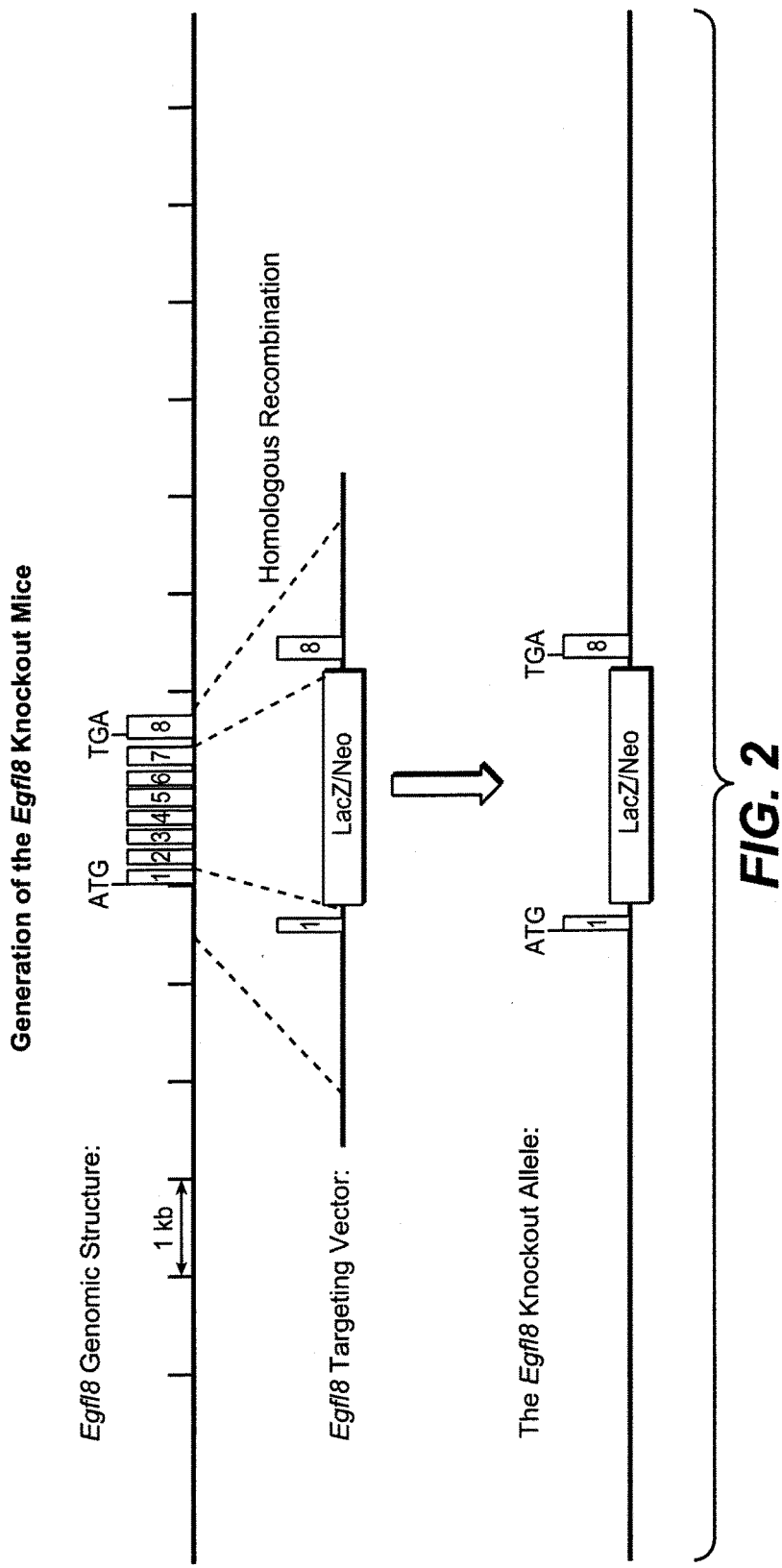
FIG. 2 shows the strategy employed to generate Egfl8 knockout mice.

A construct was made with Exons 2-7 of Egfl8 replaced with LacZ and a neomycin resistance gene and used to generate Egfl8 knockout mice using standard homologous recombination methods (see FIG. 2). The resulting knockout allele only encodes the first 35 amino acids of EGFL8, of which 28 encode the signal sequence. Egfl8 heterozygous knockout mice (Egfl8+/−) were crossed to Egfl7+/− mice (described in Schmidt et al., *Development*, 134(16): 2913-23. (2007)) to generate double homozygous mice (Egfl7−/−Egfl8−/−).

We first did wholemount staining to determine the effect of mutations in Egfl7 and/or Egfl8 on the retinal vasculature. We sacrificed postnatal day 8 mice (of different genotypes), dissected out eyeballs, and fixed them with 4% PFA in PBS (phosphate buffered saline, pH 7.4) @ 4° C., overnight. We then washed 3× in PBS, dissected out the retina and removed hyaloid vessels, and placed them in 48 or 96 well plates for staining. We permeabilized with PBST (PBS+0.5% Triton® X100) for 1 hr, and incubated the retinas with Blocking Buffer (5% Normal Goat Serum+0.5% Triton® X100+0.01% $NaN_3$ in PBS) for 2-16 hours @4° C. We removed the Blocking Buffer and then incubated with primary stain overnight at 4° C. on rotator (primary stain was biotinylated-isolectin B4: from Sigma, Cat.#=L2140. Isolectin B4 binds vascular endothelium specifically). Biotinylated isolectin B4 stock solution was made as followed: dissolve in 0.9% (0.15M NaCl) to concentration of 1 mg/ml, store small aliquots at −20° C. Use stocks as 50× (working conc.=20 μg/ml). We washed at least 6 times with PBST for 1 hour each @4° C. and then incubated with secondary stain (Streptavidin Alexa 488 (1:150) from Molecular Probes) in PBST+10% goat serum, rotate plate overnight at 4° C. We then washed at least 6 times with PBST one hour each at 4° C. on the rotator and then 1× with PBS containing DAPI. We fixed the tissue 1× with 4% paraformaldehyde in PBS for no more than 5 min and then rinsed at least 4 times with PBS until PFA is completely rinsed off of the tissue (about 30 min-1 hr).

We transferred each retina to a small Petri-dish containing PBS, cut 4-5 slits along the radial axes from the edge to about ⅔ of the radius. We placed retina on a glass slide with vitreous side up, removed as much liquid as possible, and then used a pair of forceps to flatten the retina on the slide. We then quickly added 1-2 drops of Fluoromount-G and put coverslips over the samples. If there were small folds in a retina, we gently moved the coverslip until the retina is perfectly flat. We also ensured that no bubbles were found in the tissue. We took photographs using the Zeiss confocal microscope, taking serial optical images to cover the entire thickness of each retina, and then reconstructed 3D images from the serial single frame images using Zeiss software.

Figure 3:
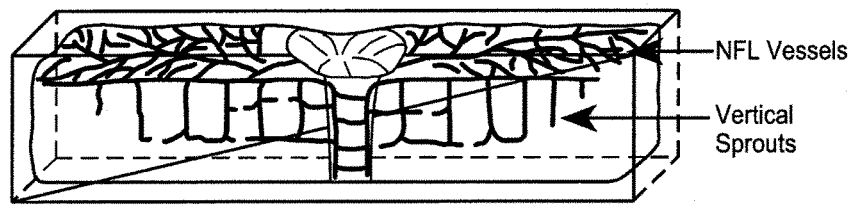
FIG. 3 shows the vascular phenotype in the retinas of Egfl7+/−, Egfl8−/− and Egfl7−/−, Egfl8−/− mice.
Figure 3:
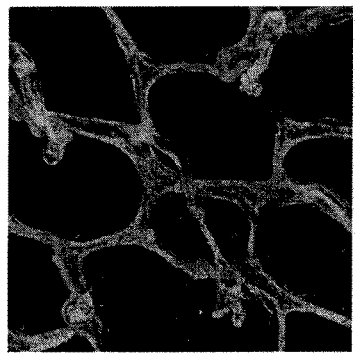
Figure 3:
Figure 3:
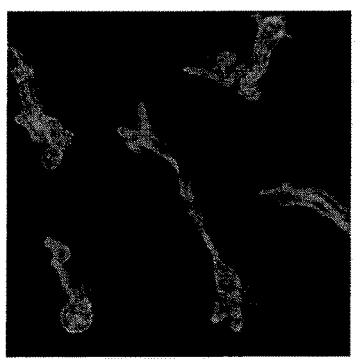
Figure 3:
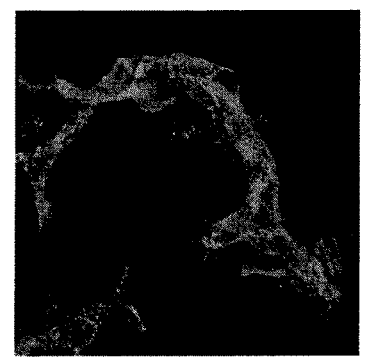

In wild-type and Egfl7−/− retina (data not shown), as well as Egfl7+/−, Egfl8−/− retina (FIG. 3, left panels), we observed normal distribution and morphology of individual vertical sprouts, which are formed by sprouting angiogenesis from the NFL vessels. However, in the Egfl7−/−, Egfl8−/− retina (FIG. 3, right panels), vertical sprouts were clustered together to form aberrantly large sprouts. Thus, these results indicated that Egfl7 and Egfl8 act together to control sprouting angiogenesis in the deeper layer of the retina. Loss of either gene alone is insufficient to cause vascular malformation.

Next we analyzed the phenotype of Egfl8 mutants in a model of angiogenesis in mouse corneas (see, e.g., Kenyon et al., *Invest. Opthalmol. Vis. Sci.* 37: 1625-32 (1996)). Aseptic technique was used throughout the procedure. Adult mice between 7-10 weeks of age were anesthetized with intraperitoneal injection of 2.5% Avertin®. In addition to general anesthesia, the eye was topically anesthetized with 0.5% proparacain (Allergan, Irvine, Calif.). Working under a surgical scope, a central, intrastromal linear keratotomy was performed with a surgical blade parallel to the insertion of the lateral rectus muscle. Using a modified von Graefe knife, a lamellar micropocket was dissected toward the temple limbus. A Hydron pellet containing bFGF (40 to 50 ng/pellet) was placed on the corneal surface at the base of the pocket with jeweler's forceps, and using one arm of the forceps, the pellet was advanced to the temporal end of the pocket, 1 mm from the limbic vessel. Antibiotic ointment (0.5% erythromycin; E. Fougera & Co) was applied to the eye, not only to prevent infection but also to decrease irritation due to the irregular ocular surface. Both eyes of the mice were utilized in our study.

Six days after pellet implantation, pictures were taken of the mouse eye using a dissection microscope (Stemi 2000-C, Zeiss) coupled with a digital camera (AxioCam MRc5, Zeiss). At the time of euthanasia, mice were perfused with 10 ml HBSS-heparin and then 10 mL of FITC-dextran/5.5 mg/mL poly-L-Lysine solution. Corneal whole mounts were made of the enucleated eyes. Images of new vessels, which had taken up the fluorescein, were taken under microscope. The neovascular area labeled by FITC as well as the cornea size were measured using computer-assisted image analysis (Image-Pro Plus 6.0, MediaCybernetics). The percentage of vascular area was calculated according to the formula: (new vascular area/size of cornea)×100.

Figure 4:
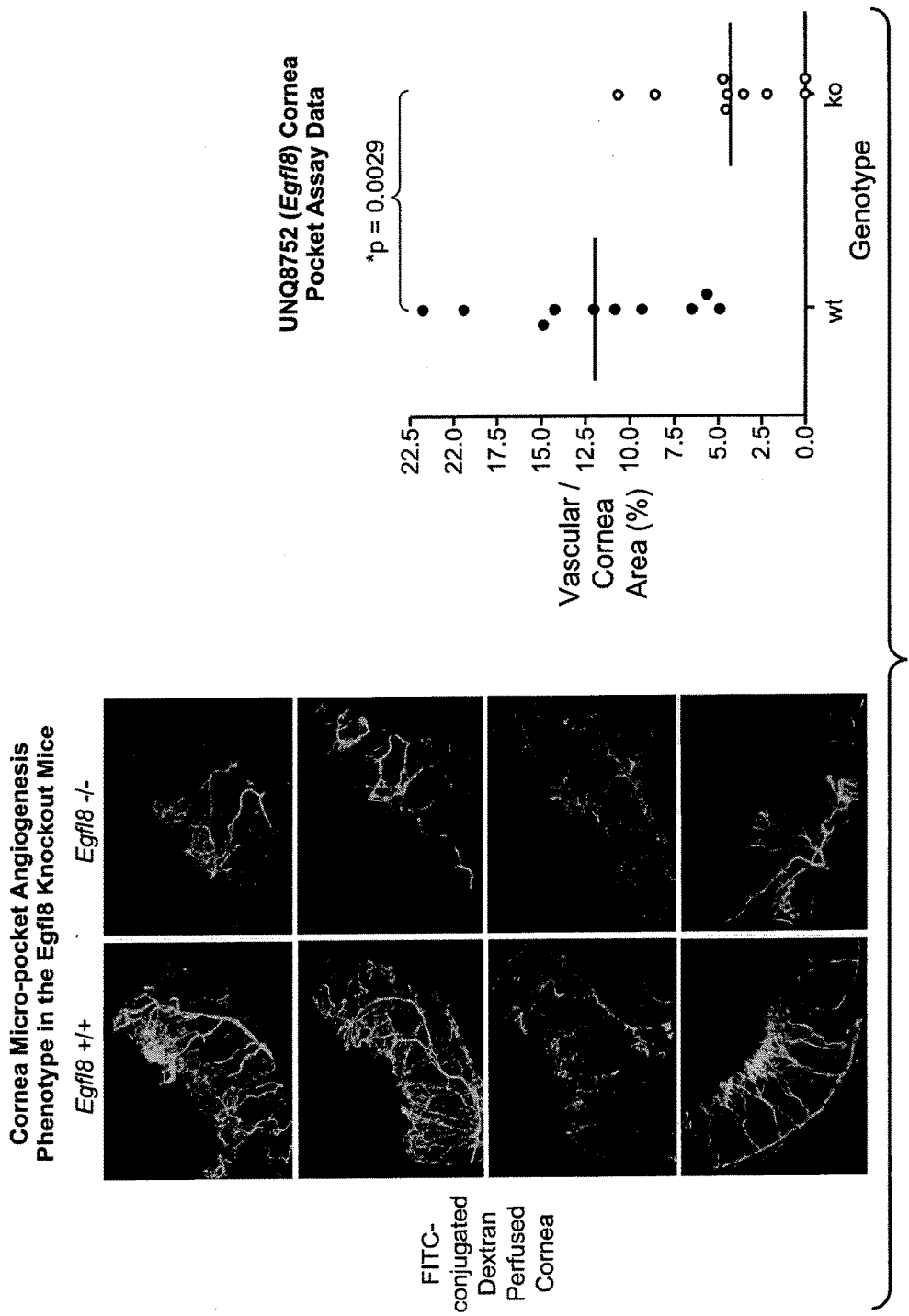
FIG. 4 shows the cornea micro-pocket angiogenesis phenotype in Egfl8 knockout mice.

We observed that corneal vascular density in Egfl8−/− mice was slightly less than half that of wild-type mice (FIG. 4). These results confirmed that Egfl8 alone plays a role in vascularization.

The foregoing written specification is considered to be sufficient to enable one skilled in the art to practice the invention. However, various modifications of the invention in addition to those shown and described herein will be apparent to those skilled in the art from the foregoing description and fall within the scope of the appended claims.

What is claimed is:

1. A method of reducing or inhibiting angiogenesis in a subject having a pathological condition associated with angiogenesis, comprising administering to the subject an EGFL8 antagonist, wherein EGFL8 has the sequence of SEQ ID NO:1 or SEQ ID NO:2, and wherein the EGFL8 antagonist is an anti-EGFL8 antibody or a fragment thereof which binds to EGFL8 and wherein the pathological condition is diabetic retinopathy, choroidal neovascularization (CVN), age-related macular degeneration (AMD), diabetic macular edema (DME), pathological myopia, von Hippel-Lindau disease, histoplasmosis of the eye, retinal vein occlusion (RVO), central retinal vein occlusion (CRVO), branched central retinal vein occlusion (BRVO), corneal neovascularization, retinal neovascularization, retinopathy of prematurity (ROP), subconjunctival hemorrhage, hypertensive retinonpathy, neovascular glaucoma or immune rejection of transplanted corneal tissue.

2. The method of claim 1, wherein the EGFL8 antagonist is an anti-EGFL8 antibody.

3. The method of claim 1, further comprising administering to the subject a second anti-angiogenic agent.

4. The method of claim 3, wherein the second anti-angiogenic agent is administered prior to or subsequent to the administration of the EGFL8 antagonist.

5. The method of claim 3, wherein the second anti-angiogenic agent is administered concurrently with the EGFL8 antagonist.

6. The method of claim 3, wherein the second anti-angiogenic agent is an anti-EGFL7 or an anti-vascular endothelial cell growth factor (VEGF) antibody.

7. The method of claim 6, wherein the anti-VEGF antibody is bevacizumab.

* * * * *